United States Patent [19]

Lorenz et al.

[11] Patent Number: 5,587,200
[45] Date of Patent: Dec. 24, 1996

[54] METHOD FOR MANUFACTURING A MEDICAL ELECTRODE

[75] Inventors: Hans P. Lorenz, Schwarzenbruk; Bernd Straehler, Berlin, both of Germany; Ulf Lindegren, Enskede, Sweden

[73] Assignee: Pacesetter AB, Solna, Sweden

[21] Appl. No.: 554,770

[22] Filed: Nov. 7, 1995

[30] Foreign Application Priority Data

Nov. 11, 1994 [DE] Germany .......................... 44 40 386.0

[51] Int. Cl.$^6$ ................ B05D 1/32; C23C 8/04; C23C 8/24; C23C 16/34
[52] U.S. Cl. ............... 427/2.24; 427/253; 427/255.2; 427/582; 427/586; 427/282
[58] Field of Search .................... 427/2.24, 2.1, 427/582, 584, 586, 253, 2.12, 255.2, 282

[56] References Cited

U.S. PATENT DOCUMENTS

| | | | |
|---|---|---|---|
| 4,595,601 | 6/1986 | Horioka et al. ................... | 427/583 |
| 4,867,223 | 9/1989 | Matsumura et al. .............. | 427/251 |
| 5,064,681 | 11/1991 | Berry et al. ....................... | 427/252 |
| 5,149,596 | 9/1992 | Smith et al. ....................... | 427/252 |
| 5,194,642 | 3/1993 | Winter et al. ..................... | 556/51 |
| 5,225,251 | 7/1993 | Esrom ............................... | 427/554 |
| 5,290,368 | 3/1994 | Gavigan et al. .................. | 427/554 |
| 5,290,608 | 3/1994 | Grunwald et al. ................ | 427/557 |
| 5,308,651 | 5/1994 | Ohta et al. ........................ | 427/582 |
| 5,385,579 | 1/1995 | Helland ............................. | 607/130 |
| 5,405,373 | 4/1995 | Petersson et al. ................. | 607/121 |
| 5,427,631 | 6/1995 | Johansson et al. ............... | 148/23.8 |
| 5,514,425 | 5/1996 | Ito et al. ........................... | 427/253 |

FOREIGN PATENT DOCUMENTS 0115778 8/1984 European Pat. Off. .

*Primary Examiner*—Diana Dudash
*Attorney, Agent, or Firm*—Hill, Steadman & Simpson

[57] ABSTRACT

In a method for manufacturing electrodes for medical applications, particularly implantable stimulation electrodes, having an active layer of porous titanium nitride, a substrate of electrically conductive material that is in an atmosphere containing titanium, nitrogen and hydrogen is irradiated with an excimer laser through an optical mask, and a structure of porous titanium nitride is deposited on the substrate.

14 Claims, No Drawings

METHOD FOR MANUFACTURING A MEDICAL ELECTRODE

BACKGROUND OF THE INVENTION

1. Field of the Invention

The invention is directed to a method for manufacturing electrodes for medical applications, particularly implantable stimulation electrodes, of the type having a active layer of porous titanium nitride.

2. Description of the Prior Art

Electrodes of the above-described type are disclosed in European Patent 0 115 778. These electrodes are composed of an electrically conductive carrier material and, in the active region, have a porous layer of a carbide, a nitride or a carbonitride of at least one of the metals titanium, vanadium, zirconium, niobium, molybdenum, hafnium, tantalum or tungsten, i.e. including titanium nitride (TiN). The known electrodes are manufactured with a physical vapor deposition (PVD) process, whereby the porous layer is applied by physical vapor deposition onto the carrier material serving as a substrate. To that end, the metal that forms the carbide, nitride or carbonitride is evaporated, for example with an electron beam evaporator, from a supply of the metal in an atmosphere containing nitrogen and/or methane and the corresponding metal compound is deposited on the substrate.

The electrodes manufactured in the way set forth above are advantageously utilized as stimulation electrodes for heart pacemakers. For specific applications, however, a heart pacemaker electrode having a structured electrode arrangement is expedient, for example, wherein two conductive regions insulated from one another are arranged concentrically relative to one another. In order to achieve a high double-layer capacitance given contact with the body fluid, it is then necessary to provide the electrode with a porous titanium nitride layer. Such an electrode configuration, however, has not yet been realized with titanium nitride electrodes.

SUMMARY OF THE INVENTION

It is therefore an object of the present invention to provide a method with which titanium nitride electrodes of the type initially set forth can be manufactured, wherein the active layer is structured, i.e. wherein a specific electrode structure is present.

This object is inventively achieved in a method wherein a substrate of electrically conductive material that is in an atmosphere containing titanium, nitrogen and hydrogen is irradiated with an excimer laser through an optical mask, and a structure of porous titanium nitride is deposited on the substrate.

Arbitrary electrode configurations can be manufactured with the method of the invention, i.e. electrodes having an arbitrary structure, for example an electrode arrangement with two concentric electrodes. For such purposes, a corresponding optical mask is produced for the desired structure and is thereby charged with laser emission, whereby a sharp imaging of the mask in the substrate plane ensues due to the laser, i.e. the mask only allows light in the form of the desired structure to pass.

If electrode structures were to be manufactured according to the conventional PVD process heretofore employed, a surface-wide coating of the substrate would have to ensue first, and this would have to be followed by an etching process matched to the titanium nitride and the substrate material—with photomasking—in order to achieve the desired electrode configuration. By contrast, a specific electrode structure can be directly produced in one working cycle in the method of the invention, which is a laser-CVD chemical vapor deposition process, i.e. a laser-induced, chemical vapor deposition, without an etching process being subsequently required.

DESCRIPTION OF THE PREFERRED EMBODIMENTS

In the method of the invention, thin layers of titanium nitride are locally photolytically deposited on a substrate; the substrate thereby remains unmodified. The deposited layers have a thickness of up to 20 μm or more, and they have a rough surface, i.e. they are porous. The sheet capacitance of these layers is higher by roughly a factor of 100 than that of a smooth titanium surface. At a frequency of 1 Hz, for example, the sheet capacitance of the laser-CVD TiN layers of the invention thus amounts to about 2.5 $mF/cm^2$ (titanium: approximately 0.025 $mF/cm^2$).

An atmosphere containing titanium, nitrogen and hydrogen serves for the deposition of the titanium nitride. This atmosphere preferably has one of the following compositions:

(a) tetrakis(dimethylamino)-titanium and nitrogen with hydrogen possibly added thereto;

(b) titanium tetrachloride, nitrogen and hydrogen;

(c) titanium tetrachloride and ammonia.

Instead of tetrakis(dimethylamino)-titanium, however, the corresponding ethyl compound, for example, can be utilized and titanium tetrabromide, for example, can be utilized instead of titanium tetrachloride. Further, nitrogen/hydrogen mixtures can be replaced by ammonia and vice versa.

The electrically conductive substrate on which the porous TiN layers are deposited is preferably composed of titanium. Alternatively, however, a substrate of, for example, platinum can be used or a substrate of other precious metals. The substrate may also be composed of metal alloys such as Elgiloy® or non-rusting steel, known as VA-steel. It is important that the substrate be physiologically compatible. The substrate, moreover, can be at elevated temperature, for example at a temperature of about 60° C., during the deposition.

In the method of the invention, the substrate is preferably irradiated with light having one of the following wavelengths: 193 nm, 248 nm, 308 nm or 351 nm. This means that the following excimer lasers are preferably utilized: ArF (193 nm), KrF (248 nm), XeCl (308 nm) and XeF (351 nm). The pulse frequency is generally 100 Hz and the pulse length is generally 20 ns.

The invention shall be set forth in further detail with reference to an exemplary embodiment.

Titanium (Ti) serves as the substrate material in a batch technique. Immediately before the coating, the Ti substrates are cleaned with ethanol and with a hydrogen HF plasma and are arranged in a reaction chamber through which tetrakis-(dimethylamino)-titanium, nitrogen and hydrogen are conducted (overall pressure: 10 mbar). The irradiation ensues with an XeF excimer laser (wavelength: 351 nm; pulse frequency: 100 Hz; energy flux density: 162 $mJ/cm^2$). The substrate can be heated to a temperature of 60° C.

TiN layers having a thickness of about 13 μm are obtained under these deposition conditions given a deposition time of 20 minutes (deposition rate: 40 μm/h).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for manufacturing a medical electrode comprising the steps of:

disposing a bare substrate of electrically conductive material in an atmosphere containing titanium, nitrogen and hydrogen;

directly covering said bare substrate with an optical mask having a pattern therein having openings corresponding to a structure to be produced on said substrate; and irradiating said substrate with said optical mask thereon in said atmosphere with an excimer laser and thereby depositing a structure of porous titanium nitride corresponding to said pattern directly on said substrate exclusively in said openings.

2. A method as claimed in claim 1, wherein the step of disposing a substrate of electrically conductive material in an atmosphere containing titanium, nitrogen and hydrogen comprises disposing said substrate of electrically conductive material in an atmosphere of titanium tetrachloride, nitrogen and hydrogen.

3. A method as claimed in claim 1, wherein the step of disposing a substrate of electrically conductive material in an atmosphere containing titanium, nitrogen and hydrogen comprises disposing a titanium substrate in an atmosphere containing titanium, nitrogen, and hydrogen.

4. A method as claimed in claim 1, wherein the step of irradiating said substrate with said optical mask thereon in said atmosphere with an excimer laser comprises irradiating said substrate with said optical mask thereon in said atmosphere with an excimer laser which emits laser radiation having a wavelength selected from the group consisting of 193 nm, 248 nm, 308 nm, and 351 nm.

5. A method as claimed in claim 1, comprising the additional step of elevating a temperature of said substrate during irradiation of said substrate with said excimer laser.

6. A method for manufacturing a medical electrode comprising the steps of:

disposing a substrate of electrically conductive material in an atmosphere containing tetrakis(dimethylamino)-titanium and nitrogen;

covering said substrate with an optical mask having a pattern therein corresponding to a structure to be produced on said substrate; and irradiating said substrate with said optical mask thereon in said atmosphere with an excimer laser and thereby depositing a structure of porous titanium nitride corresponding to said pattern on said substrate.

7. A method as claimed in claim 6, wherein the step of disposing a substrate of electrically conductive material in an atmosphere containing tetrakis (dimethylamino)-titanium and nitrogen comprises disposing said substrate of electrically conductive material in an atmosphere containing tetrakis (dimethylamino)-titanium and nitrogen and hydrogen.

8. A method as claimed in claim 6, wherein the step of disposing a substrate of electrically conductive material in an atmosphere containing tetrakis (dimethylamino)-titanium and nitrogen and comprises disposing a titanium substrate in said atmosphere containing tetrakis (dimethylamino)-titanium and nitrogen.

9. A method as claimed in claim 6, wherein the step of irradiating said substrate with said optical mask thereon in said atmosphere with an excimer laser comprises irradiating said substrate with said optical mask thereon in said atmosphere with an excimer laser which emits laser radiation having a wavelength selected from the group consisting of 193 nm, 248 nm, 308 nm, and 351 nm.

10. A method as claimed in claim 6, comprising the additional step of elevating a temperature of said substrate during irradiation of said substrate with said excimer laser.

11. A method for manufacturing a medical electrode comprising the steps of:

disposing a bare substrate of electrically conductive material in an atmosphere containing titanium tetrachloride and ammonia;

directly covering said bare substrate with an optical mask having a pattern therein having openings corresponding to a structure to be produced on said substrate; and irradiating said substrate with said optical mask thereon in said atmosphere with an excimer laser and thereby depositing a structure of porous titanium nitride corresponding to said pattern directly on said substrate exclusively in said openings.

12. A method as claimed in claim 11, wherein the step of disposing a substrate of electrically conductive material in an atmosphere containing titanium tetrachloride and ammonia comprises disposing a titanium substrate in said atmosphere containing titanium tetrachloride and ammonia.

13. A method as claimed in claim 11, wherein the step of irradiating said substrate with said optical mask thereon in said atmosphere with an excimer laser comprises irradiating said substrate with said optical mask thereon in said atmosphere with an excimer laser which emits laser radiation having a wavelength selected from the group consisting of 193 nm, 248 nm, 308 nm, and 351 nm.

14. A method as claimed in claim 11, comprising the additional step of elevating a temperature of said substrate during irradiation of said substrate with said excimer laser.

\* \* \* \* \*